United States Patent [19]

Humphrey

[11] 4,113,363

[45] * Sep. 12, 1978

[54] PROCESS AND APPARATUS FOR ASTIGMATIC AND SPHERICAL SUBJECTIVE TESTING OF THE EYE

[75] Inventor: William E. Humphrey, Orinda, Calif.

[73] Assignee: Humphrey Instruments, Inc., San Leandro, Calif.

[*] Notice: The portion of the term of this patent subsequent to Mar. 30, 1993, has been disclaimed.

[21] Appl. No.: 790,203

[22] Filed: Apr. 25, 1977

Related U.S. Application Data

[63] Continuation of Ser. No. 670,810, Mar. 26, 1976, abandoned, which is a continuation-in-part of Ser. No. 452,232, Mar. 18, 1974, Pat. No. 3,947,097.

[51] Int. Cl.$^2$ ............................................. A61B 3/02
[52] U.S. Cl. ....................................... 351/17; 351/34; 351/39
[58] Field of Search .............................. 351/17, 34, 39

[56] References Cited

U.S. PATENT DOCUMENTS

| | | | |
|---|---|---|---|
| 3,785,723 | 1/1974 | Guyton | 351/34 |
| 3,841,760 | 10/1974 | Guyton | 351/39 X |
| 3,947,097 | 3/1976 | Humphrey | 351/17 |

*Primary Examiner*—Paul A. Sacher
*Attorney, Agent, or Firm*—Townsend and Townsend

[57] ABSTRACT

An apparatus and process for determining subjective astigmatic and spherical prescription for the eye is disclosed. A target, consisting of a line of small angular divergence, is focused for maximum clarity by the adjustment of spherical optics, causing the line to become proximate to the retinal viewing plane of the eye. Change of astigmatic correction is made along at least one axis diagonal to the line target until maximum sharpness of the line results, without resultant spherical change and resultant movement of the image away from the retinal plane of the eye being tested. A second target, again consisting of a line of small angular divergence, is introduced; this line target is angularly inclined to the first target, preferably at 45°. Spherical adjustment is made to obtain subjective line sharpness. Change of astigmatic correction is made along at least one axis diagonal to the line target until maximum sharpness of the line results, without resultant spherical change and resultant movement of the image away from the retinal plane of the eye. By the expedient of vector analysis of the two astigmatic components, astigmatic correction can either be plotted on Cartesian coordinates (in accordance with a technique recently developed), or conversion to the more conventional polar description of astigmatism using cylinder power and rotation can occur.

15 Claims, 18 Drawing Figures

FIG_1

FIG_2

FIG_3

FIG_4

FIG_5

FIG_12

FIG_6

FIG_9

FIG_7  FIG_8

FIG_10

FIG_11

FIG_13

FIG_15

FIG_14b  FIG_14a    FIG_16b  FIG_16a

PROCESS AND APPARATUS FOR ASTIGMATIC AND SPHERICAL SUBJECTIVE TESTING OF THE EYE

This is a continuation of application Ser. No. 670,810, filed Mar. 26, 1976, now abandoned, which was a continuation-in-part application of copending Patent Application Ser. No. 452,232, filed Mar. 18, 1974, now U.S. Pat. No. 3,947,097, issued Mar. 30, 1976.

FIELD OF THE INVENTION

This invention relates to subjective eye testing apparatus for determining astigmatism and spherical correction.

SUMMARY OF THE PRIOR ART

Subjective measurement of astigmatism has heretofore related to patient focus on a radial array of spoke-like lines. Best spherical lens correction is determined. Additional positive shpere is added. The spoke line appearing sharpest is the one nearest one of the required astigmatism axes. Negative cylinder can be added at 90° to the orientation of the sharper line until all lines are of similar sharpness. The process may be repeated with variations known to those skilled in the art. Finally, when the astigmatic correction reaches sufficient precision, other optimizing techniques such as the employment of a Jackson crossed cylinder may be introduced.

These prior art techniques have several disadvantages. First, the patient must be sufficiently instructed by the eye examiner to look for the spoke or other linear target having the optimum visual appearance. The process of instructing the patient and getting the patient to understand the instruction is time consuming and to portions of the population extremely difficult. This is because of the presence of visual aberrations, lack of visual coordination, or absence of basic intelligence and experience (as, for example, in the case of young children).

Additionally error, especially at low diopter cylinder power, can occur.

Finally, the patient is inhibited in responding to such conventional tests by his own expected predelections to size and shape. Adjustment in sphere produces resultant change in size; the patient, not accustomed to resultant change in size, confuses desired optical clarity with preventing undesired size change. Erroneous spherical prescription can result.

Similarly, adjustments in cylinder produce resultant change in target geometry; the patient, not accustomed to resultant change in target geometry, confuses desired optical clarity with preventing undesired target geometry change. Erroneous cylindrical presecriptions can result.

BRIEF DESCRIPTION OF THE INVENTION

An apparatus and process for determining subjective astigmatic and spherical prescription for the eye is disclosed. A target, consisting of a straight line, is focused for maximum clarity by the adjustment of spherical optics, causing the line to become proximate to the retinal viewing plane of the eye. Change of astigmatic correction is made along at least one axis diagonal to the line until maximum sharpness of the line results, without resultant spherical change and resultant movement of the image away from the retinal plane of the eye being tested. A second target, again consisting of a straight line, is introduced. This line target is angularly inclined to the first target, preferably at 45°. Spherical adjustment is made to obtain subjective line sharpness. Change of astigmatic correction is made along at least one axis diagonal to the line until maximum sharpness of the line results, without resultant spherical change and resultant movement of the image away from the retinal plane of the eye. By the expedient of vector analysis of the two astigmatic components, astigmatic correction can either be plotted on Cartesian coordinates (in accordance with a technique recently developed), or conversion to the more conventional polar description of astigmatism using cylinder power and rotation can occur.

It has been shown that measurement of astigmatism can be determined and plotted at two components 45° one with respect to another. By plotting such components on a 360° chart, rotation and power of cylinder (especially low power cylinder) can easily be determined. See Patent Application Ser. No. 263,329, filed June 15, 1972, entitled "Ophthalmological Apparatus and Process Having Independent Astigmatic and Spherical Inputs", now William E. Humphrey U.S. Pat. No. 3,822,932.

A specialized multi-line target created by 4 to 12 diopter cylinder smear consists of point sources disposed at the three apexes of a triangle. By utilizing the cylinder to smear the point sources normal to the base of the triangle and measuring astigmatism along at least one diagonal component of measurement inclined with respect to the axis of the smearing cylinder, an array of three lines is generated. Since astigmatic viewing, when corrected along one component of astigmatic measurement, results in all three smeared lines being equidistant one from another, an astigmatic test results which enables the patient to equidistantly space a central smeared line from the remaining smeared lines. The ability to center or align line segments, commonly known as Vernier visual acuity, is possessed by large samples of the population.

An additional multi-line target array preferably consisting of three lines all having small angular divergence (say, in the order of 7.5°) can be used for fine correction of the astigmatic components detected by the procedures herein. By the expedient of applying a smearing cylinder of predetermined orientation — preferably of 2 diopters — smearing of all the diverging lines will occur; however, the line or lines along the direction of smear will still appear sharp for a person of normal vision. Since one of the diverging lines will presumably be aligned to the direction of patient astigmatism in combination with the astigmatism of the smearing cylinder, this one line will appear with optimum clarity.

By the expedient of responding to examiner questions and designating the line of optimum clarity, the patient can furnish the examiner with sense and rough amount of correction necessary for the complete removal of astigmatic error. By appropriate adjustment of smearing cylinder power and line divergence, optimum views of different lines in the array can be equated to a power and sense of correction required. For example, where the smearing cylinder is 2 diopters and the line divergence 7.5°, the patient preference of one line in a three line array over an immediately adjacent line gives an indicated astigmatic correction of approximately ½ diopter, while the position of the sharper line or lines indicates the sense of the required correction.

FURTHER OBJECTS AND ADVANTAGES OF THIS INVENTION

An object of this invention is to disclose a process and apparatus for determining astigmatism and spherical prescription with each measurement being determined in isolated components.

An advantage of determining astigmatism in two isolated components in accordance with the apparatus and process of this invention is that the adjustment of one component of astigmatism does not affect the adjustment of the remaining component of astigmatism.

A further advantage of the apparatus and process of this invention is that adjustment of the spherical input is independent of both of the astigmatic components of this invention. Change of the spherical prescription does not require correspondent change in either of the determined astigmatic prescriptions.

It should be noted that the spherical prescription is completely determined at an unexpected place in this test. Immediately before the determination of the second astigmatic component, spherical prescription is determined. Thus, the unexpected sequence of prescription of this test is first to determined one astigmatic component of correction for a patient's eye; second, to determine the total spherical component necessary for correction of the patient's eye; and finally, to determine the remaining astigmatic component for correction of a patient's eye.

It should be further noted that each line target requires adjustment of only two, and not three optical components. Each line target requires adjustment of the spherical component, and that astigmatism component which varies astigmatism diagonally to the orientation of the straight line target. Adjustment of that astigmatism component which varies astigmatism parallel and perpendicularly to the orientation of the straight line target is not made.

An advantage of each straight line target is that it requires adjustment only to its correspondent variable astigmatism component and the variable spherical component. Surprisingly, these adjustments can be made in any order.

A further object of this invention is to vastly simplify the instruction to the patient. The patient is only told to optimize the view of a straight line using discrete spherical and astigmatic controls. Room for confusion with other imaging phenomena, such as changes in shape and size, is completely eliminated.

A further advantage of this invention is not only the product of vastly simplified instructions to the patient, but additionally the product of the discrete and independent spherical and astigmatic adjustments. Adjustment of any one of the three optic inputs (one spherical input and two astigmatic inputs) is completely independent of the remaining optical adjustments. No interrelated adjustment is required.

A further object of this invention is to disclose simplified straight line targets for viewing by the patient, the target always consisting of at least one straight line.

An advantage of using a straight line target is that with spherical power change, no disturbing magnification change occurs to the patient. The patient can change his acuity with respect to a straight line without disturbing size changes which tend to inhibit his subjective response to the optical test.

A further advantage of the straight line target used with this invention is that with astigmatic corrections, no disturbing shapes changes occur to the patient. In viewing a straight line, the patient sees an unchanging target save and except for the optical clarity with which the target is seen.

An object of this apparatus and process is to provide an instrument with an image which is coherent to measure astigmatism in two separate components only.

An advantage of the image produced is that while astigmatism in one component is measured, astigmatism error in the remaining astigmatism component is completely obscured. The image, being only sensitive to one component of astigmatism, can determine that component of astigmatism with a high degree of accuracy, and with a minimum of confusion, as the test is specific to a particular type of astigmatism component.

A further advantage of measuring astigmatism in separate components is that a plot of the components to determine ultimate astigmatic prescription in cylinder power and rotation can be made with greater ease and higher degrees of accuracy than is now conventional.

Yet another advantage of the apparatus and process of this invention is that it can easily be constructed in the form of a hand-held instrument, or alternately easily inserted in and used with existing optical testing equipment.

Yet another object of a specialized cylinder smeared line target of this invention is to couple the measurement of astigmatism to patient Vernier visual acuity.

An advanage of utilizing patient Vernier visual acuity for subjective measurements of astigmatism is that high degrees of Vernier visual acuity are possessed by large segments of the population, and that line centering possesses information as to which direction additional increments of adjustment must be made.

An additional object of this invention is to disclose a combination of a multi-line target and smearing cylinder for the precision adjustment of astigmatic error. A multi-line target is used having small angles of divergence (say, in the order of 7.5°) between adjacent lines. The target is viewed through the disclosed variable astigmatic optics of this invention combined with a small smearing cylinder in the order of 2 diopters. By the selection of the line having the optimum visual clarity, the patient can give the examiner an indication of first the power of astigmatic correction required, and second the sense of astigmatic correction required.

An advantage of this aspect of the invention is that the examiner can bracket the optimum astigmatic prescription in discrete steps. With each discrete step, the examiner is given an indication of both the incrememt and sense of correction required for future bracketing and final optimizing of the prescription.

An advantage of this aspect of the invention is that the residual of astigmatic correction can be gradually and systematically reduced to accuracies approaching 1/16 diopter.

A further advantage of this fine tuning technique is that low power smearing cylinder is used. The degree of precision required for angular alignment of the smearing cylinder is reduced over higher power smearing cylinders which must be precisely aligned.

Yet another advantage of the line target array is that it has a distant advantage for analyzing vision defects in the presence of corneal irregularities. Where corneal irregularities are present, line targets consisting of smeared point sources of light may produce apparent curved lines to the patient. This is because the lens of the eye — including the corneal irregularity of the eyes — are all part of a lens system which together produce the smeared line. By the expedient of eliminating the point source of light and substituting a line source, the corneal irregularity can be averaged away in an optimum astigmatic prescription.

DESCRIPTION OF THE DRAWINGS

Other objects, features and advantages of this invention can be more fully understood, reference being had to the following specification and attached drawings in which.

Figure 1:
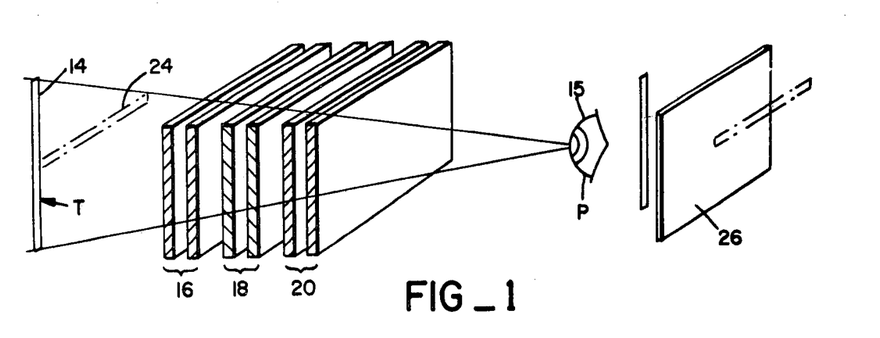
FIG. 1 is a schematic perspective view of the eye test device of this invention, schematically illustrating a target, a patient's eye viewing the target, and the corrective optics intermediate the target and the patient's eye, and a schematic representation in planar form of the retinal plane of the patient's eye.

Referring to FIG. 1, a schematic diagram in partial perspective illustrating an apparatus which can be used for the practice of the process of this invention is illustrated. Viewing the perspective and schematic view from left to right, a target T consisting of a straight line 14 is first illustrated. Typically, straight line 14 is a line of one minute of arc or less to the patient's eye (this dimension being at the maximum of visual acuity of the eye) although coarser targets may also be useful. The target T can be generated in any number for conventional ways, from the conventional eye chart to projections and the like.

The patient P, schematically illustrated at eye 15, views target T through corrective optics. Responsive to his visual clarity of the target being viewed, adjustment is sequentially the real image from both simple and compound magnifiers to the field mirror, the optics of the field mirror are essentially confined to a relay of the stop or exit pupil. The optics of the mirror do not participate in the magnification and hence do not generate appreciable coma, astigmatism, spherical aberrations, and distortion associated with the off-axis use of a conventional spherical field mirror. Provision for centering of the eye at the relayed stop or exit pupil is disclosed.

It will be realized that this application relates to a monocular remote microscope rather than a stereo remote microscope.

The invention claimed in this application includes a microscope for projecting a magnified image of an object to an eye of a viewer at a location in space removed from said object, said microscope comprising: a magnifier having a magnifier stop, said magnifier addressed to said object at a distance to project an image of said object at a preselected distance away from said magnifier; a field mirror aligned to receive the projected image of said magnifier in substantially the plane of said mirror and to receive the light of said image at a first off-axis angle with respect to the axis of said field mirror; and, said field mirror disposed with respect to said eye of said viewer to relay the light of said image at a second and complementary off-axis angle along a magnified view path to the eye of said viewer and to relay to a conjugate location of said field mirror in space the stop of said magnifier so that the eye of said viewer when positioned at said relayed stop receives a view of said object equivalent to the light emanating from said stop of said magnifier as collected by said field mirror.

It will be appreciated that the drawings of this patent application will suffice to describe my other referenced patent made to the spherical optic lens pairs 16 (for the first time), the first astigmatic power lens pair 18, the spherical optic lens pairs 16 (for the second time), and finally to the second astigmatic power lens pair 20.

Spherical optic lens pairs 16 are known. (See U.S. Pat. No. 3,305,294, issued Feb. 21, 1967, entitled "Two Element Variable Power Spherical Lens" to Luis W. Alvarez and U.S. Pat. No. 3,507,565 issued Apr. 21, 1970, entitled "Variable Power Lens and System" to Luis W. Alverez and William E. Humphrey.)

Broadly, spherical optic lens pairs 16 are moved relatively one to the other responsive to the subjective patient manifestations of visual acuity of target T. The spherical optics move gradually and continuously to generate either positive spherical power or negative spherical power by relative movement of one lens element 16 relative to the other lens element 16.

First and second astigmatic optics 18 and 20 are known. (See U.S. Pat. No. 3,751,138, issued Aug. 7, 1973, to William E. Humphrey, entitled "Variable Anamorphic Lens and Method for Constructing Lens".)

Regarding lens pairs 16, 18 and 20, the reader should realize that these are extremely complex optical surfaces. These extremely complex surfaces are here schematically shown as flat pieces of glass. Their complex surfaces can only be understood after referring to the referenced U.S. Pat. Nos. 3,305,294; 3,507,565; and 3,751,138.

Broadly, first astigmatic optic lens pairs 18 are moved relatively one to the other responsive to subjective patient manifestations of visual acuity of target T. First astigmatic lens pairs 18 change the astigmatic power or focal lenght from positive to negative along one diagonal and simultaneously change the astigmatic lens power from negative to positive along the remaining diagonal. Opposite relative horizontal movement produces opposite astigmatic adjustments.

Likewise, second astigmatic lens pairs 20 are moved relatively one to the other responsive to subjective patient manifestations of visual acuity of target T. Second astigmatic optics 20 change the astigmatic power or focal length from positive to negative along the vertical axis and simultaneously from negative to positive along the horizontal axis upon relative movement of each of the lenses of the lens pairs in relative horizontal movement. Opposite relative horizontal movement produces opposite astigmatic adjustments.

It should be noted at this juncture that much of the mechanical equipment which can be used to supplement the operation of this embodiment of this invention has been disclosed elsewhere. For example, apparatus for causing equal and opposite movement to lens pairs 16, 18 and 20 is described in my copending Patent Application Ser. No. 371,809, filed June 20, 1973, entitled "Eye Test Apparatus", now U.S. Pat. No. 3,874,932.

Likewise, it will soon hereinafter be disclosed that relative movement of each of the three separate lens pairs is capable of generating optic prescriptions. Mechanism for the remote generation of both adjusted spherical optic output and astigmatic prescription output is set forth in my copending Patent Application Ser. No. 263,329, filed June 15, 1972, entitled "Ophthalmological Apparatus and Process Having Independent Astigmatic and Spherical Inputs", now U.S. Pat. No. 3,822,932.

Before proceeding further with the description of this invention, one aspect of the first embodiment illustrated in FIGS. 1-5 should be made clear. The variable astigmatic lens element pairs 18 and 20 are of the type that produce perpendicularly crossed positive and negative astigmatic lens power along axes normal one to another. While the lens elements here illustrated are preferred, it is apparent that other lenses and optic apparatus could be used for generation of this effect. For example, see my copending Patent Application Ser. No. 263,329, filed June 15, 1972, entitled "Opthalmological Apparatus and Process Having Independent Astigmatic and Spherical Inputs", now U.S. Pat. No. 3,822,932.

Having set forth the rather simple mechanics of this invention, operation of the process and apparatus for the generation of the subjective eye test of this invention can now be understood by first understanding optical limitations relating to astigmatism.

First, it will be well to emphasize why only straight line targets consisting of preferably a single straight line or at least a plurality of parallel straight lines are used.

Referring to FIG. 1, it will be noted that target T is shown as a single straight line 14 of exaggerated width extending in the vertical direction. An imaginary line 24, shown in broken horizontally extending lines, is also shown. Focus of these lines relative to the imaginary and schematically shown retinal plane 26 of eye 15 of patient P will help understand the function of the variable astigmatic lens pairs 18 and 20 of this invention.

Assume that the eye 15 of the patient P has an appreciable astigmatic aberration. It is in the nature of astigmatism that straight lines of certain orientations will focus at different distances relative to retinal plane 26 of eye 15. In the view here shown, the aberration of the patient P causes the imaginary horizontal line 24 to focus behind the imaginary retinal plane 26 and the vertical straight line 14 to focus in front of the imaginary retinal plane.

Clearly, if the corrected astigmatic view is to be made of either the line targets 14 or 24, differing spherical corrections will be required to bring into focus and view either of the line targets 14 or 24. Understanding this, it should be doubly clear that the spoke-like multilined targets of the prior art cannot be satisfactorily used with this invention. As different lines of different angular orientation have different planes of best focus in the vicinity of the retinal plane 26 of a patient P having astigmatism, affording completely different patient viewing, only line targets having parallel lines can be satisfactorily used.

Second, once a straight line target, such as straight line target 14, is focused to the focal length of an eye 15 having astigmatic aberration, astigmatic adjustment should be made along a plane that will not cause relative movement of the focal length of the viewed line with respect to the retinal viewing plane of the eye. Stated in other terms, astigmatism power adjustments should be made along normally disposed axes in equal positive and negative powers on each respective axis, these normally disposed axes being substantially 45° from the angle of the target. Thus, astigmatic correction in such a component can be made without affecting the overall focal length of the astigmatism target.

Having these precepts explained and understood, the basic manipulative process of this invention can be explained with sequential reference being made to FIGS. 1-5 of the drawings.

Referring to FIG. 1, patient P is asked to view line 14. Thereafter, relative movement of the spherical lens elements 16 is made responsive to maximum or optimum visual acuity of line 14. Movement of the line to coincidence with the retinal plane 26 of the patient P results as is illustrated in FIG. 2.

Figure 2:
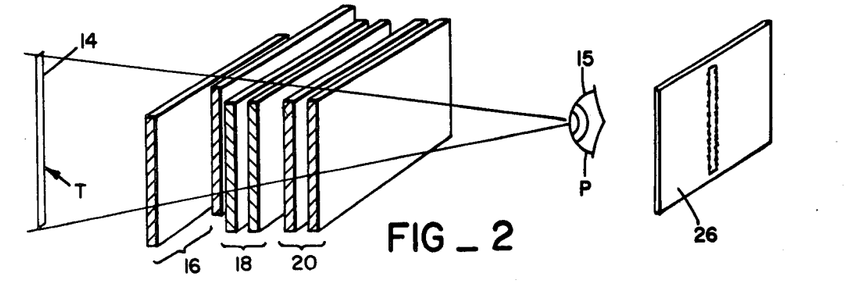
FIG. 2 is a view similar to FIG. 1 illustrating the first spherical power adjustment of this invention.

As shown in the extreme right of FIG. 2, line 14 does not appear with its full optical clarity. This is because the ambient astigmatism of the patient P along diagonals relative to straight line 14 causes the edges thereof to be blurred. It therefore remains to correct these astigmation aberrations without causing resultant spherically related movement of line 14 out of the retinal plane 26.

Figure 3:
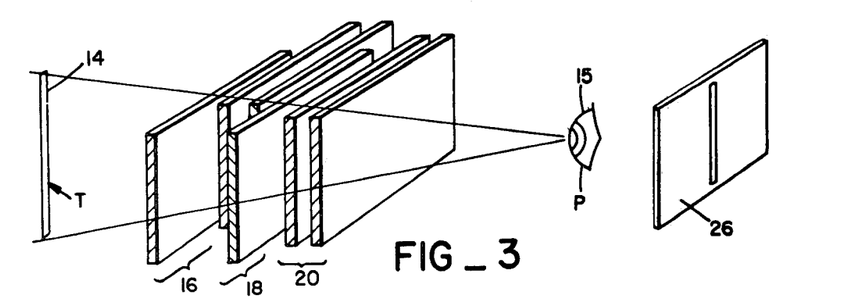
FIG. 3 is a view similar to FIG. 1 illustrating the determination of the first component of astigmatic correction of this invention.

Referring to FIG. 3, second astigmatic lens pairs 18 have been moved relative to one another to cause optimum visual sharpness to patient P. Since first astigmatic lens pairs produce correspondent negative and positive or positive and negative astigmatic lens power along perpendicular axes — each of which is diagonal to vertical straight line target 14 — subjective improvement of the visual acuity of line target 14 results without any change in the focal length. This adjustment produces the final astigmatic prescription for one component of astigmatism (the only qualification being that it may be desirable to repeat the entire sequence herein to optimize the optical settings).

Figure 4:
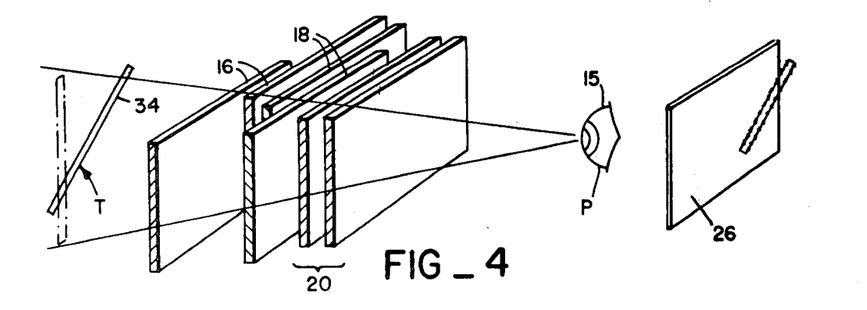
FIG. 4 is a view similar to FIG. 1 illustrating an angularly inclined (preferably at 45°) new target with the second and final spherical prescription change being made to determine the spherical prescription required for the patient.

Referring to FIG. 4, a new line target 34 has been placed for patient viewing. Preferably, this line target should be at an altered alignment of 45° with respect to the target 14. It should be noted, however, that precise 45° alignment change of the target is not required. Changes in target alignment of more than 30° can produce tolerable results.

Referring to FIG. 4, and remembering the sequence of FIGS. 1-3, it will be remembered the astigmatic aberration of eye 15 of patient P will cause the new line target 34 to have a different focal length with respect to the imaginary retinal focal plane 26 of eye 15. Therefore, a second spherical correction will be made at spherical lens pairs 16. This adjustment will be made responsive to maximum patient visual acuity of new line target 34 and will cause the focal impingement of the line target 34 to fall on the retinal plane 26.

A surprising result occurs at this juncture of the process of this invention. The second adjustment of sphere to coincide straight line target 34 with retinal plane 26 causes the final spherical power to be known. This occurs even though the final astigmatic component is not known. Moreover, determination of the final astigmatic component will not effect the final spherical setting of the illustrated instrumentation, although transformation of the prescriptions obtained herein to the more accepted prior art prescription will result in the adjustment of sphere merely because of the presence of the changing cylinder.

It should be remembered with respect to FIG. 4, that spherically optimizing the view of straight line target 34 leaves visual astigmatic clarity yet to be obtained. Stated in other words, patient P at eye 15 does not get the optimum clarity of his view line 34 because of the presence of the uncorrected astigmatic horizontal and vertical astigmatic components.

Figure 5:
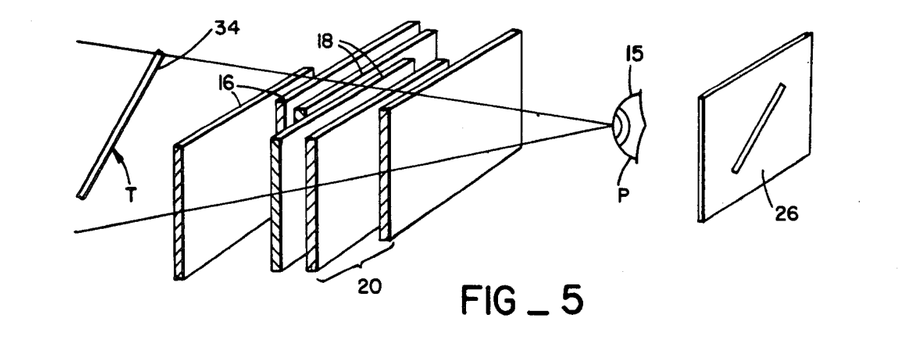
FIG. 5 is a view similar to FIG. 4 illustrating the determination of the final astigmatic component with completion of the resultant test.

Referring to FIG. 5, second astigmatic optic lens pairs 20 are translated one to another responsive to maximum visual acuity. The final component of astigmatism is obtained. Again, since the respective negative and positive or positive and negative axes of astigmatic power adjustment are at substantial 45° alignment to straight line target 34, no resultant movement off of the retinal plane 26 can occur. Moreover, this adjustment is the final adjustment in the process of this invention giving the final coordinate of the desired astigmatic prescription.

Having explained the process of this invention, it should be made clear that the sequence of steps herein set forth can be repeated. This may be done to optimize the prescription obtained or alternately to check prescription accuracy.

It should also be understood that the physical positioning of lens pairs 16, 18 and 20 may be permuted, if desired, without invalidating the procedure.

It should be noted that each line target 14 of FIGS. 1-3 and 34 of FIGS. 4-5 requires adjustment of only two, and never three optical components. Thus, for target 14, only spherical optics 16 and first astigmatic optics 18 are adjusted; second astigmatic optics 20 are not adjusted.

Likewise for target 34, only spherical optics 16 and second astigmatic optics 20 are adjusted; first astigmatic optics 18 are not adjusted.

It should also be appreciated that for each target, it does not make any difference in what order adjustment occurs. The spherical optics can be adjusted prior to the adjustment of the applicable astigmatic optics. Conversely, the applicable astigmatic optics can be adjusted prior to the adjustment of the spherical optics.

It is surprising to note that in the manipulation of either the spherical optics 16 or the astigmatic optics 20 for target 34, the final prescription results. This is true whether spherical optics 16 are first manipulated, or astigmatic optics 20 are first manipulated.

Having set forth this first and preferred embodiment of the invention, attention can now be given to an alternate embodiment.

Figure 6:
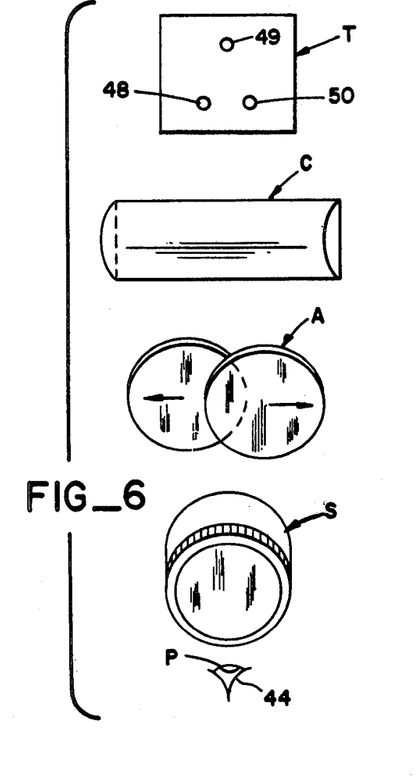
FIG. 6 is a perspective view of an alternate embodiment using cylinder smear of point sources of light for the measurement of one component of patient astigmatism.
Figure 9:
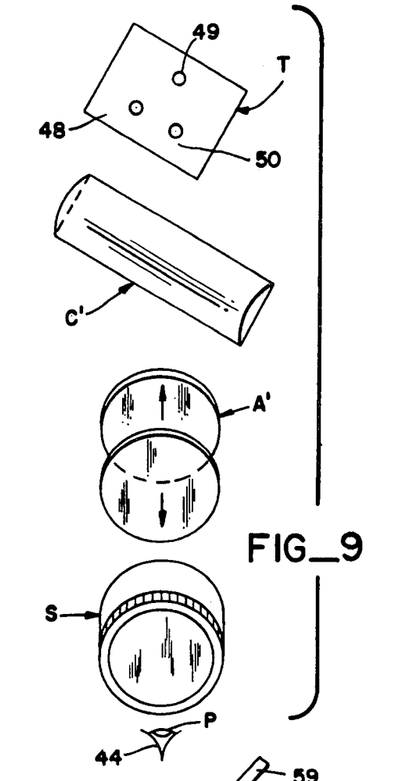
FIG. 9 is a view of the apparatus of FIG. 6 illustrating the smearing cylinder and target of this invention aligned at 45° with respect to the alignment shown in FIG. 6 for testing of the remaining component of patient astigmatism.
Figure 10:
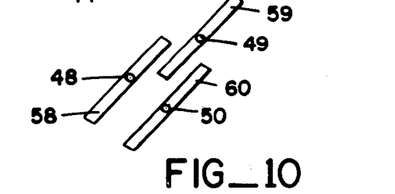
FIG. 10 is a patient's eye view of the target through the apparatus disclosed where astigmatic prescription along the remaining component of astigmatic acuity has been determined.

With reference to FIG. 6, a patient P at a patient viewing station looks along a light path through adjustable spherical optics S, adjustable power cylindrical optics A, constant cylinder optics C, and onto target T. Typically, the adjustable power cylindrical optics are varied so that the patient P obtains a view of the target T which is similar to that shown in FIG. 7. By collating the power of adjustable astigmatic correction required to have target T appear as a patient view similar to the view of the target shown in FIG. 7, one component of astigmatism can be measured. The remaining component of measurement is measured by the same device aligned as illustrated in FIG. 9. Typically, patient P views realigned target T through adjustable spherical optics S, adjustable power astigmatic optics A', and realigned constant optic cylinder C'. A patient view of target T with corrected astigmatic prescription along the remaining component is illustrated in FIG. 10.

Figure 12:
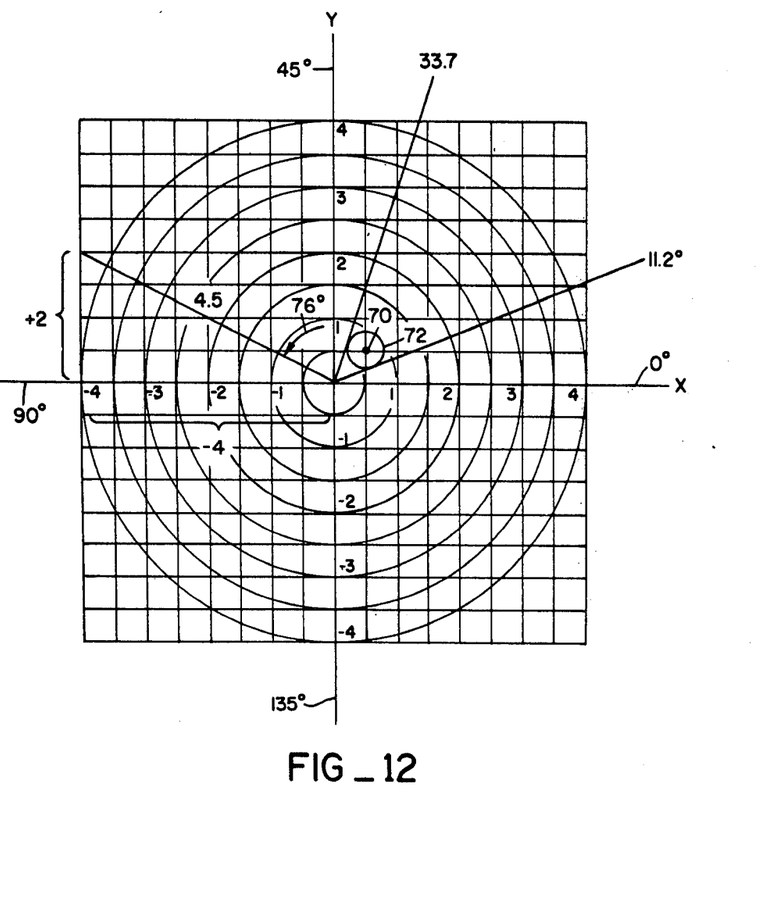
FIG. 12 is a graphic plot illustrating how astigmatic measurements can be combined on the plot to prescribe rotation and power of cylindrical alignment.

Thereafter with respect to FIG. 12, plotting of the two measured astigmatic inputs can be made to prescribe cylinder power and cylinder rotation.

Having generally set forth this embodiment of the invention, attention can now be given in some detail.

Patient P is schematically shown by an eye 44. Typically the measure of astigmatism of the patient will relate to irregularities of the patient's eye. Therefore, it must be understood that the patient angular alignment remains unchanged. The permanent optic cylinder and target only are realigned to determine a second component of astigmatism.

Adjustable spherical optics S can take any conventional form as well as the previously described variable focus optics. Typically, Galilean type optics can be used.

Target T is illustrated at the far end of the optical instrument. It is shown containing three point sources 48, 49 and 50. Preferably, these point sources are point sources of light, the light being provided by background illumination through the target T (the background illumination not being shown).

Constant cylinder optics C are shown somewhat exaggerated. The cylinder optics here are shown aligned horizontally with respect to patient P and have a strong diopter power in the vertical direction. As illustrated herein, cylinder optics C are of approximately 12 diopters.

In actual practice the cylinder power of cylinder C can vary within wide limits. For example, cylinder power ranges within 4 and 20 diopters can be used.

Variable astigmatic lenses A are of the type shown and described in William E. Humphrey U.S. Patent Application Ser. No. 235,134 filed Mar. 16, 1972, and entitled "Variable Anamorphic Lens and Method for Constructing Lens", now U.S. Pat. No. 3,751,138, issued Aug. 7, 1973. As is set forth in great detail in that disclosure, variable astigmatic optics can be obtained by moving specially constructed lens elements horizontally and vertically one with respect to another. Utilizing the lens configuration alignment and relative movement illustrated in FIGS. 5 and 6 of the above entitled patent, astigmatism correction at 45° with respect to the horizontal axis of cylinder C can be obtained.

It should be understood that variable astigmatic lenses A are here shown schematically as flat circular discs of glass. Only by reference to the above referenced U.S. Pat. No. 3,751,138 can the extremely complex surface of these lenses be fully understood.

It should also be understood that virtually any apparatus designed for producing variable power astigmatic correction will work with this invention. For example, the counter-rotating negative and positive cylindrical lenses described and set forth in Patent Application Ser. No. 263,329, filed June 15, 1972, filed by William E. Humphrey, and entitled "Ophthalmological Apparatus and Process Having Independent Astigmatic and Spherical Inputs", now U.S. Pat. No. 3,822,932 can be used. It is only required that the variable astigmatism be produced at an angle oblique to the axis of cylinder C. It is preferred that the astigmatism produced by the variable astigmatic lens elements A be at 45° with respect to cylinder C.

Having set forth the simple construction of this apparatus, its operation can now be explained.

With the instrument orientation as shown in FIG. 6, patient P views target T through strong cylindrical optic C. Cylinder C will blur the respective point sources 48–50 of target T into a series of respective straight lines 58–60 (see FIG. 2). First spherical correction is made to the eyes of patient P to secure optimum view of the borders of lines 58, 59 and 60. This spherical adjustment brings the lines into coincidence with the retinal plane, as in the manner previously illustrated in FIG. 2. Remembering that the point sources are disposed at the imaginary apexes of an isosceles triangle, and assuming for the purposes of elementary description that no astigmatic prescription is required, the point sources will appear largely as they are illustrated with respect to FIG. 7. Specifically, point source 48 will be blurred to a line 58, point source 49 will be blurred to a line 59, and point source 50 will be blurred to a line 60.

Changing the assumption relating to eye 44 of patient P, the operation of the device to obtain one component of astigmatic prescription can now be explained. Assume that the eye of patient P includes an astigmatic aberration. Moreover, this astigmatic aberration has a component at 45° relative to the axis of cylinder C of +1 diopters of power and a component at right angles of −1 diopter. The target T, in the absence of any astigmatic input at variable astigmatic optics A, would appear as it does in FIG. 8 to patient P. Line 59' will appear close to line 60', and relatively spatially removed from line 58'.

Variable astigmatic optics C will next be manipulated responsive to patient visual Vernier acuity of target T. Specifically, paired variable astigmatic elements A would be translated one with respect to another to produce a 2 diopter astigmatism correction at a rotational alignment 45° from the rotational alignment of cylinder C. Lines 58', 59' and 60' shown in FIG. 8 would tend to move to the position 58, 59 and 60 shown in FIG. 7 upon the achievement of correct astigmatic prescription. Line 59 will be equidistantly spaced from lines 58 and 60.

Figures 7, 8:
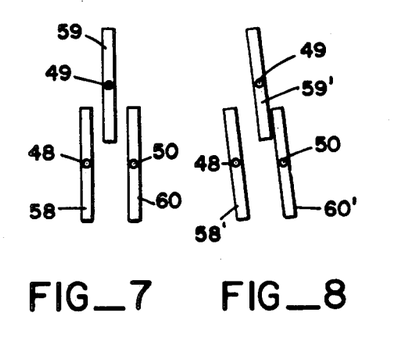
FIG. 7 is a patient's eye view of the preferred target of this invention when optimum astigmatic correction has been achieved.
FIG. 8 is a view of the same target where optimum astigmatic prescription has not been achieved.

Focusing attention on the target configurations of FIGS. 7 and 8, the Vernier acuity provided by the configuration of target T can be explained. Vernier acuity includes the ability of human beings to visually establish alignment or centering of lines. With respect to FIG. 8, it will be remembered that the combined astigmatism in the eye 44 of patient P at 45° to the axis of cylinder C and the power of cylinder C incline the blurred lines 58', 59' and 60' of point sources 48, 49 and 50 respectively. This inclination caused line 59' to move closer to line 60'. Simultaneously, line 58' moved further away from line 59'.

It might be expected that adding astigmatism to the view-path would blur the lines, requiring a frequent readjustment of the sphere power to maintain sharp lines. However, this is not the case. The addition of astigmatism diagonal to the "smeared" lines only changes the orientation of the cylindrical smearing and not its strength or spherical component, at least to a good approximation for the angular variation usually involved.

The patient has variable power astigmatic optics A adjusted to establish equidistant spacing from the lines generated by the smeared point sources of light 48, 49 and 50. Upon adjustment, to compensate for his astigmatic component at 45° with respect to the axis of cylinder C, the lines from point sources of light 48, 49 and 50 will be equidistantly spaced.

Human beings with any kind of visual acuity can normally space three lines one from another to an equidistant spacing with very high degrees of accuracy. This is herein referred to as Vernier accuity.

During the measurement of cylinder power at an angle which is 45° with respect to the cylindrical alignment of cylinder C, it should be understood that the relatively strong power of cylinder C blocks astigmatism perpendicular and parallel to its alignment. While patient astigmatism in this component may cause blurred lines 58–60 to become slightly longer or shorter, changes in the length of these lines will be substantially not perceptible to the patient.

It has been found that particularly with yound patients having large amounts of visual accommodation, large inputs of subconscious sphere correction can occur. Consequently, and especially with younger patients, the variable spherical optics S are gradually moved to the largest positive power for which the lines remain sharp. This causes ultimate cancellation of subconscious focusing and assures reliability of the test.

Having set forth the measurement of astigmatism in one component, the measurement of astigmatism in the remaining component will occur with the instrument alignment shown in FIG. 9.

Regarding the instrument alignment as shown in FIG. 9, patient P remains in the same real world alignment for view through the apparatus of FIG. 9 as he does for view through the apparatus of FIG. 6. Likewise, spherical optics S illustrated in FIG. 9 remain unchanged.

Cylinder C is realigned. Typically, it is aligned to a new position C' where its axis is preferably inclined 45° with respect to the original position shown in FIG. 6 (although alignment changes up to 30° will again produce tolerable results). In this position, the strong power of cylinder C' neutralizes or overwhelms all components of astigmatism perpendicular and normal to its rotational alignment. It thus can be understood that the components of astigmatism originally measured are completely neutralized in the second test.

Target T' is similarly rotated. Point sources 48, 49 and 50 are aligned relative to one another at a new angle 45° with respect to the alignment of target T shown in FIG. 6. Target T' has an alignment identical to the alignment of cylinder C'. Point sources 48, 49 and 50 are all located at the apexes of an imaginery triangle having its base parallel to the rotational alignment of cylinder C'.

Variable astigmatic lenses A, it will be remembered, are of the type shown and described in William E. Humphrey Patent Application Ser. No. 235,134, filed Mar. 16, 1972, and entitled "Variable Anamorphic Lens and Method for Constructing Lens", now U.S. Pat. No. 3,751,138 issued Aug. 7, 1973. Utilizing the lens configuration, alignment, and relative movement illustrated in FIGS. 3 and 4 of the above entitled patent, astigmatism correction vertically and horizontally which is 45° with respect to the axis of cylinder C can be obtained.

Just as in the previous illustration of the apparatus of FIG. 6, virtually any apparatus designed for producing variable astigmatism correction will work with the invention. It is only required that the variable astigmatism be produced at an angle oblique the axis of cylinder C. It is of course preferred that the astigmatism be produced by the variable astigmatic lens elements A' at 45° with respect to the alignment of cylinder C'.

Having realigned the instrument from the orientation shown in FIG. 6 to the orientation shown in FIG. 9, the process of measuring the remaining component of astigmatism can now be described.

As in the previous case, patient P views target T' through a strong cylinder optic C'. Cylinder C' will blur the respective point sources 48-50 of target T' into a series of respective straight lines 58-60. First, spherical correction is made to secure optimum view of the borders of lines 58, 59 and 60. It will be remembered that the point sources are disposed at imaginary apexes of an isosceles triangle. Assuming for the purpose of the elementary description that no spherical prescription is required along a horizontal or vertical component located at 45° with respect to the axis of cylinder C', the point sources will appear largely as they are illustrated with respect to FIG. 10. Specifically, point source 48 will be blurred to a line 58, point source 49 will be blurred to a line 59, and point source 50 will be blurred to a line 60.

Figure 11:
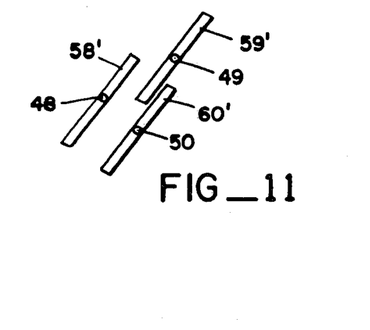
FIG. 11 is a view of the target where correct astigmatism correction has not been determined.

Changing the assumption relating to eye 44 of the patient P, the operation of the device to obtain the remaining component of astigmatism prescription can now be explained. Assume that the eye of the patient P includes an astigmatic aberration. Moreover, this astigmatic aberration has a horizontal component at 45° relative to the axis of C of $-2$ diopters of cylinder power and a vertical component of $+2$ diopters of cylinder power. The target T, in the absence of any astigmatic input at variable astigmatic optics A, would appear as it does in FIG. 11 to patient P. Lines 59' will appear close to line 60', and relatively spatially removed from line 58'.

Variable astigmatic optics A' will next be manipulated responsive to patient visual Vernier acuity of target T'. Specifically, paired variable astigmatic elements A' would be vertically translated one with respect to another to produce a 4 diopter crossed cylinder ($\pm$) 2 diopters along orthogonal axes at a rotational alignment of 45° from the rotational alignment of cylinder C'. Lines 58', 59' and 60' shown in FIG. 11 would tend to move to the position 58, 59 and 60 shown in FIG. 10 upon achievement of correct astigmatic prescription. Line 59 will be equidistantly spaced from lines 58 and 60.

It should be realized that the second embodiment of the invention here shown will admit of a number of modifications. For example a two point source target could be used with the smearing cylinder aligned to present to the astigmatically corrected eye a single straight line. The astigmatically uncorrected eye would view more than one straight line. Upon the introduction of astigmatic correction, alignment of the lines into a single straight line would be the simple subjective visual goal for the patient. Thus, this embodiment of the invention will admit of the use of any number of targets having a plurality of straight lines provided the lines can move into a recognizable geometric alignment upon movement of the corrective astigmatic optics.

As in the case of the previous embodiment, only two and never three of the optical components are manipulated for each target. Thus, for target T, orientation of FIGS. 6–8 only, adjustment of spherical optics and horizontal relative movement of variable astigmatic optics A and never vertical relative movement of variable astigmatic optics A is required. Likewise, for target T', orientation of FIGS. 9–11 only, adjustment of spherical optics and vertical relative movement of variable astigmatic optics A' and never horizontal relative movement of variable astigmatic optics A' is required.

Likewise, for each orientation of target T, it should also be appreciated that it does not make any difference in what order adjustment occurs. The spherical optics S can first be adjusted. Alternately, astigmatic optics A can first be adjusted.

Moreover, it is surprising to note that the first manipulation of either the spherical optics S or the astigmatic optics A for the second orientation of target T results in the final prescription. This is true whether spherical optics S are first manipulated or astigmatic optics A are first manipulated.

Having obtained the two components of astigmatism utilizing the test device of this invention, the use of the device to obtain the required prescription can now be determined. Referring to FIG. 12, the Cartesian coordinate plot converts to conventional cylindrical lens angle. However, the cylindrical lens angle has been doubled or multiplied by a factor of 2. Thus, in the plot illustrated in FIG. 12, 180° of cylindrical lens rotation appears over 360° of actual coordinate plot. Referring to FIG. 12, it can be seen that the compensating astigmatism setting of the test of the apparatus aligned at FIG. 9 should be plotted as $-4$ diopters astigmatism along the zero degree (x) direction and the compensating astigmatism setting of the test aligned as shown in FIG. 6 should be plotted as $+2$ diopters astigmatism along the 45° (y) direction, resulting in an astigmatism determination requiring a total of a 4.5 diopter cylindrical lens adjustment to the prescription at an angle of approximately 77°.

The particular lens setting used here is an extreme lens setting. Very few optical corrections are required that are this strong. This particular illustration is given here so that the polar coordinate plot of this invention may be set forth and thereafter understood.

It will be understood that the particular form of Cartesian coordinates used here has an additional advantage. Specifically, at low diopter power a conventional polar coordinate system prescription of astigmatic lenses becomes unwieldly. This inconvenience is due to the margin of error and the fact that the error increases with respect to angular rotation as lower diopter lens corrections are required.

An example of the error plotted into these coordinates can be helpful. Assume that the test apparatus of FIG. 6 and FIG. 9 has resulted each in one half of a diopter of positive cylinder correction. Assume further that the uncertainty of the measurement could be $\pm \frac{1}{4}$ diopter.

Referring to FIG. 12, it can be seen that the $\frac{1}{2}$ diopter position has been plotted at 70. Moreover, the area of possible error in the $\frac{1}{2}$ diopter prescription has been plotted at 72. Assuming that the visual error of the patient in the astigmatic correction could fall anywhere within the circle 72, it can be seen that the polar coordinate plot produces a large error in angular description. For example, assuming that the point derived from the instrument was to fall somewhere within the circle 72, the angle of that circle could range between 11.2° and 33.7°.

The conversion of the plots to a Cartesian coordinate system not only has the capability of being readily translatable into the older and more conventional cylindrical optical description of angle of rotation and diopter power, but can be used in a method in itself to describe astigmatic optical correction. This method, both in mathematical theory and apparatus is set forth and claimed in Patent Application Ser. No. 263,329, filed June 15, 1972, and entitled "Ophthalmological Apparatus and Process Having Independent Astigmatic and Spherical Inputs", now William E. Humphrey U.S. Pat. No. 3,822,932, and my copending Patent Application Ser. No. 385,748, now abandoned in favor of Continuation Patent Application Ser. No. 483,171, filed June 26, 1974, entitled "Apparatus for Ophthalmological Prescription Readout". It should be apparent to the reader that obvious alterations can be made to this invention. Cylindrical optics C, variable astigmatic optics A, and target T, as well as spherical lens S can all be changed at will, provided that the principles set forth herein are practiced.

Figure 13:
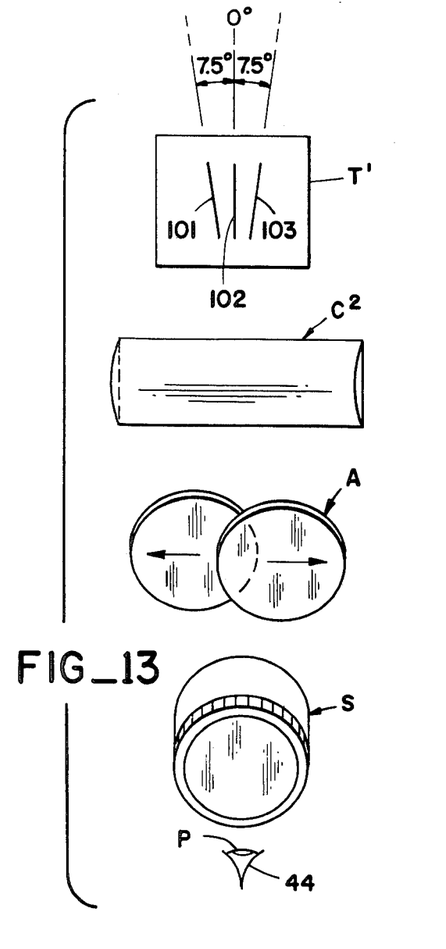
FIG. 13 is perspective view of the apparatus of this invention adapted for fine correction of astigmatic vision in an astigmatic compound of 45°–135° through the addition of a diverging line target array and a smearing cylinder of small power.
Figure 15:
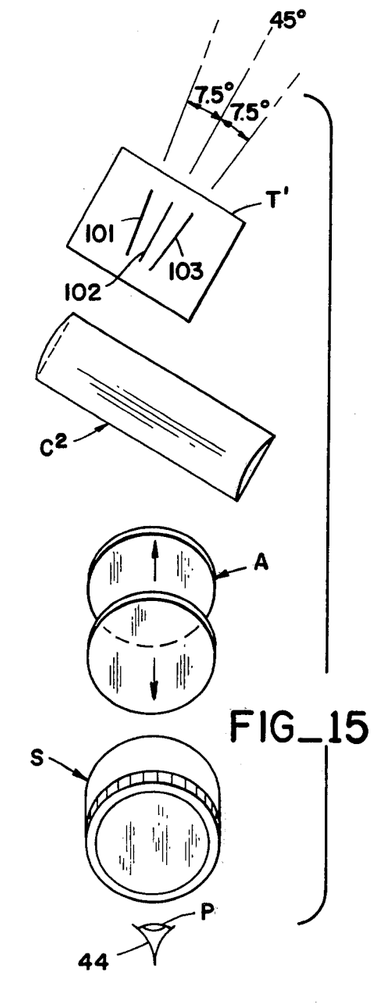
FIG. 15 is a view of the apparatus of FIG. 13 of this invention adapted for the fine correction of the remaining astigmatic component of 0°–90° through the addition of a second diverging line target array and a second smearing cylinder — both the array and cylinder being at a preferred 45° angle to that alignment illustrated in FIG. 13.

It has been found preferable to used a specialized target array and smearing cylinder to isolate residual astigmatism and rapidly reduce such residual astigmatism in each of the components used in this apparatus and process. Such isolation preferably occurs after sphere and cylinder correction have been established to a moderate degree of acuity using either of the presently described target materials or other methods illustrated with respect to FIGS. 1-12. Apparatus for this isolation of residual astigmatic component is illustrated in FIGS. 13 and 15. This apparatus will first be described.

The method of astigmatism isolation including the patient's eye view of the target will thereafter be illustrated with the inclusion of the patient's eye view of FIGS. 14a, 14b, 16a and 16b.

With reference to FIG. 13, a patient P at a patient viewing station looks along a light path through adjustable spherical optics S, adjustable cylindrical optics A, constant cylinder optics $C^2$ and target $T^1$.

A detailed description of the constant cylinder optics $C^2$ and the target $T^1$ is in order. Constant cylinder optics $C^2$ are of relatively low power. They can be in the range of 1 to 6 diopters of power and are preferably here shown at 2 diopters.

Target $T^1$ consists of an array of angularly diverging lines 101, 102 and 103. Typically, this array is contained on a screen, a projected real image, or any apparatus which produces an image for view by eye 44 of patient P along the view path beyond the cylinder $C^2$ and variable astigmatic optics A.

A preferred embodiment of an array of three lines 101, 102 and 103 is here illustrated. As can be seen, the lines angularly diverge one from another. Preferably, line 102 is aligned to the 0° axis. Lines 101 and 103 diverge at angles of 7½° on either side, with the divergence of 7½° being preferred. It should be understood that divergence up to 20° between the individual lines is operable.

The apparatus of FIG. 15 is analogous. Cylinder $C^2$ is there shown realigned. It is realigned at a preferred 45° axis with respect to the alignment of FIG. 13. Similarly, the target $T^1$ has been realigned. It is realigned at an axis of 45° with respect to the alignment shown in FIG. 13.

It is very important to note that this realignment shown in the apparatus of FIG. 15 is an arbitrary alignment which occurs without regard to any suspected principal meridian in a patient's eye. As has been set forth heretofore, the variable astigmatic optics A provide a corrective input which accommodates the astigmatic component of vision so that the target $T^1$ of FIG. 13 and the target $T^1$ of FIG. 15 is capable of view. The view of these targets is obtained irrespective of any suspected axis of astigmatism of eye 44 of patient P.

Operation of the fine tuning target $T^1$ in combination with smearing cylinder $C^2$ can be easily understood. First, using the techniques illustrated with respect to FIGS. 1-12, sphere and cylinder correction are roughly established to a moderate degree of acuity. This is done using the previously described target material or other methods within the scope of the disclosure with respect to FIGS. 1-12 or other methods known to practitioners of ophthalmic eye care. Secondly, the apparatus of FIG. 13 is first interposed. Patent P at eye 44 will first optimize any residual spherical correction using variable spherical optics S. Thereafter, patient P will view target $T^1$ with adjustment being made to astigmatic lenses A. Relative movement of the paired lens elements A in the horizontal direction will be understood to adjust the degree of 45°-135° astigmatism. The patient will perform the required adjustment until one of the lines of the target array T appears optimally sharp. A possible example of the appearance of the target is shown in FIG. 14a.

Figures 14A, 14B:
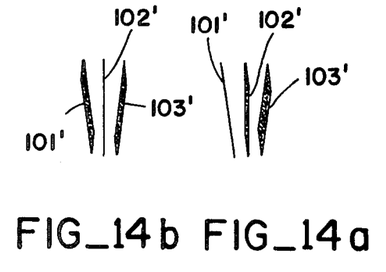
FIG. 14a is a patient's eye view of the diverging line target of FIG. 13 where optimum fine correction of astigmatism has not yet occurred and error exists in the amount of ½ diopter of astigmatism component at 45° to the center of the three lines.
FIG. 14b is a patient's eye view of the diverging line target where optimum fine correction of the first component of astigmatism has occurred.

Referring to FIG. 14a, lens elements A have been moved horizontally relative one to another. The patient has discovered that line 101' is optimally sharp. Lines 102' are blurred. This effect has occurred because the ambient astigmatism in the patient's eye combined with the astigmatic optics A and the smearing cylinder $C^2$ have smeared lines 101, 102 and 103. Line 101, however, has been smeared along its axis. It therefore retains apparent visual linear precision to the patient P.

The other lines (lines 102' and 103') have not been smeared along their axis. They have been smeared at an angle to their axis. These lines become fuzzy.

By utilizing the preferred 2 diopter smearing cylinder $C^2$ and by maintaining a 7.5° angular divergence between the lines, an unusual result occurs. The error in the astigmatic component of correction can be determined both as to sense and magnitude of correction. In the example here shown, the preference of the patient for line 101' over line 102' indicates that a ¼ diopter astigmatic component correction of the 45°–135° type is required, and in a sense such as to cause the line 102' to become sharp while 101 blurs. This sense of correction can be determined empirically or be deduced with the aid of charts such as FIG. 12.

Assuming variable astigmatic optics A are moved to produce this correction, the target will appear to the patient as illustrated in FIG. 14b. Line 102' will become optimally sharp with lines 101' and 103° becoming blurred.

It should be apparent that by changing the angle of divergence or changing the power of the smearing cylinder $C^2$, the variation of power of a selected diverging line target can be changed. For example, it has been found with varying angular line divergences of a target array that astigmatism components of this invention can be located with a precision of up to 1/16 diopter with repeatable results on the eye 44 of a patient P.

It will be remembered that the astigmatic components of this invention are independent, one from another. Thus, when the 45°–135° astigmatic component has been determined following the process of FIG. 13, it remains fixed. The apparatus of FIG. 15 can thereafter be used to tune the 0°–90° astigmatic component.

Figure 16A:
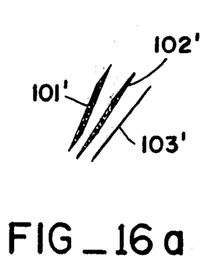
FIG. 16a is a patient's eye veiw of the diverging line target array of FIG. 15 where optimum fine correction of astigmatism has not yet occurred and error exists in the amount of ½ diopter of astigmatism component at 45° to the center of the three lines; and, FIG. 16b is a patient's eye view of the diverging line target where optimum fine correction of the second and final component of astigmatism has occurred.
Figure 16B:
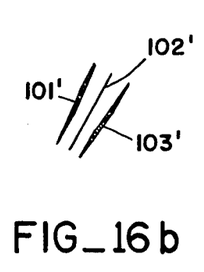

Referring to FIG. 16a, the eye 44 of patient P in viewing the apparatus of FIG. 9 is seen to prefer line 103' over lines 102' and 101' (the latter lines being blurred by smearing in a direction not axially aligned with their length). By the expedient of making a ¼ diopter correction with variable astigmatic optics A of sense such as to produce increased clarity in the direction of line 102', the array of FIG. 16b as viewed by the patient P will result. Line 102' will appear optimally sharp.

It should be understood that with respect to the target array $T^1$, the target arrays there shown with respect to FIG. 13 could be aligned at 0° or 90°. Similarly, and with respect to FIG. 15, the target arrays there shown could be aligned at 45° or 135°. Moreover, the order of astigmatic component determination does not have to be utilizing the apparatus of FIG. 13 first and FIG. 15 second. It could just as well be reversed.

It should be understood that the particular diverging line targets here shown can take a number of different patterns. For example, a first group of parallel lines could be used for line 101; a second group of parallel lines for line 102; and a third group of parallel lines for line 103. Moreover, although three lines produce a simple target to work with, it will be understood that the target array can utilize a minimum of two lines. The maximum number of lines which can be used is limited only practically by the number of lines a patient can discriminate. Additionally, line patterns of different spacing or angular array may be employed, or differing colors may be used, and so forth.

I claim:

1. A process for determining optometric prescription for the eye in at least one astigmatic component including the steps of: providing a patient viewing station; providing a first line target of first arbitrary preselected angular alignment without regard to any suspected principal axis of the patient's eye to a view path from said patient viewing station at least to said target, said first line target including small angular divergence in the range of up to 20° from said arbitrary angular alignment; providing in said view path a constant power cylinder between said patient viewing station and said first target in the range of 1 to 6 diopters aligned normally to said first arbitrary preselected angular alignment; providing in said view path variable astigmatic optics for varying astigmatic lens power along first intersecting diagonals at substantially equal and opposite angles from the preselected angular alignment of said first line target; said first variable astigmatic optics varying said astigmatic power from positive to negative along one axis of said first intersecting diagonals, and from negative to positive along the other axis of said first intersecting diagonals; and, varying the first variable astigmatic optics responsive to subject patient visual acuity of said first line target to obtain a first component of astigmatic prescription for said patient.

2. The process of claim 1 and including the step of having said patient identify one portion of said line of said target from other portions of said line of said target to indicate a magnitude and sense of correction required for said astigmatic component.

3. The process of claim 1 and wherein the divergence between said lines is 7½°.

4. The process of claim 1 and wherein said power of said constant power cylinder is 2 diopters.

5. The process of claim 1 and including the step of providing a second line target of second arbitrary preselected angular alignment without regard to any suspected principal axis of the patient's eye to a view path from said patient viewing station at least to said target, said second line target having an alignment at least 30° different from the alignment of said first line target and further including small angular divergence of said line target in the range of up to 20° from said arbitrary angular alignment; realigning in said view path said provided constant power cylinder normally to the arbitrary angular alignment of said second line target; and, varying said astigmatic optics responsive to subject patient visual acuity of said second line target to obtain a second component of astigmatic prescription for said patient.

6. The process of claim 1 and including providing variable spherical optics between said patient viewing station and said line target; and, varying said variable spherical optics to obtain an optimum view of said line target.

7. Apparatus for determining optometric prescription for the eye in at least one component of astigmatism comprising: a patient viewing station; a line target of first arbitrary preselected angular alignment without regard to any suspected principal axis of a patient's eye viewing along a view path from said patient viewing station at least to said target; said target including plurality of straight line targets small angular divergence between at least some portions of said line target in the range of up to 20° from said arbitrary angular alignment; a constant power cylinder placed in said view path between said patient viewing station and said target, said constant power cylinder having a power in the range of between 1 to 6 diopters aligned normally to said first arbitary preselected and angular alignment; variable astigmatic optics for varying astigmatic lens power along first intersecting diagonals at substantially equal and opposite angles from the preselected angular alignment of said first line target; and, said first variable astigmatic optics varying said astigmatic power from positive to negative along one axis of said first intersecting diagonals and from negative to positive along the other axis of said first intersecting diagonals.

8. The invention of claim 7 and wherein the small divergence is 7½°.

9. The apparatus of claim 7 and wherein said constant power cylinder is 2 diopters.

10. The apparatus of claim 7 and including variable spherical optics between said patient viewing station and said targets.

11. The apparatus of claim 7 and wherein all of said lines of said target diverge by a small angular divergence.

12. In the combination of an apparatus for determining optometric prescription for the eye in a component of astigmatism including a patient viewing station, a target having at least one line for view from said viewing station; a constant power cylinder placed in said view path between said patient viewing station and said target aligned normally to the arbitrary preselected angular alignment of said target; and, variable astigmatic optics for varying astigmatic lens powers along first intersecting diagonals at substantially equal and opposite angles from the preselected angular alignment of said first line target, said first variable astigmatic opitcs varying said astigmatic power from positive to negative along one axis of said first intersecting diagonals, and from negative to positive along the other axis of said first intersecting diagonals, the improvement to said constant power cylinder and target comprising: a constant power cylinder in the range of 1 to 6 diopters, and said target comprising a plurality of line targets including small angular divergence between at least some portions of said line target in the range of up to 20° from said arbitrary angular alignment.

13. The combination of claim 12 and including varying the small angular divergence of said line target to obtain discrete sense and power of astigmatic components upon patient preference of one of said portions of said target from the remaining portions of said target.

14. The combination of claim 12 and including three lines in said target, each of said lines having said small angular divergence.

15. The combination of claim 12 and wherein no two lines of said target are parallel.

* * * * *